(12) United States Patent
Wassmer et al.

(10) Patent No.: US 9,353,136 B2
(45) Date of Patent: May 31, 2016

(54) PROCESS FOR PREPARING (METH)ACRYLAMIDO-FUNCTIONAL SILANES BY THE REACTION OF AMINOALKYL ALKOXYSILANES WITH ACRYLIC ACID ANHYDRIDE

(71) Applicants: Christian Wassmer, Hausen (DE); Burkhard Standke, Loerrach (DE); Thomas Schlosser, Inzlingen (DE); Regina Krause, Rheinfelden (DE)

(72) Inventors: Christian Wassmer, Hausen (DE); Burkhard Standke, Loerrach (DE); Thomas Schlosser, Inzlingen (DE); Regina Krause, Rheinfelden (DE)

(73) Assignee: EVONIK DEGUSSA GmbH, Essen (DE)

( * ) Notice: Subject to any disclaimer, the term of this patent is extended or adjusted under 35 U.S.C. 154(b) by 0 days.

(21) Appl. No.: 14/395,735

(22) PCT Filed: Feb. 25, 2013

(86) PCT No.: PCT/EP2013/053674
§ 371 (c)(1),
(2) Date: Oct. 20, 2014

(87) PCT Pub. No.: WO2013/156188
PCT Pub. Date: Oct. 24, 2013

(65) Prior Publication Data
US 2015/0090930 A1    Apr. 2, 2015

(30) Foreign Application Priority Data
Apr. 20, 2012  (DE) .................. 10 2012 206 509

(51) Int. Cl.
| | | |
|---|---|---|
| C07F 7/18 | (2006.01) | |
| C03C 25/40 | (2006.01) | |
| C08G 77/388 | (2006.01) | |
| C08L 83/08 | (2006.01) | |

(52) U.S. Cl.
CPC ................. C07F 7/184 (2013.01); C03C 25/40 (2013.01); C07F 7/1836 (2013.01); C07F 7/1892 (2013.01); C08G 77/388 (2013.01); C08L 83/08 (2013.01)

(58) Field of Classification Search
CPC ...... C07F 7/184; C07F 7/1836; C07F 7/1892; C03C 25/40; C08L 83/08; C08G 77/388

USPC .................................. 556/419; 252/182.3
See application file for complete search history.

(56) References Cited

U.S. PATENT DOCUMENTS

| | | |
|---|---|---|
| 3,249,461 A | 5/1966 | Te Grotenhuis |
| 3,900,679 A | 8/1975 | Marzocchi |
| 5,885,341 A | 3/1999 | Standke et al. |
| 6,641,870 B2 | 11/2003 | Bartkowiak et al. |
| 6,767,982 B2 | 7/2004 | Standke et al. |
| 7,834,073 B2 | 11/2010 | Standke et al. |
| 8,039,110 B2 | 10/2011 | Jenkner et al. |
| 8,101,682 B2 | 1/2012 | Standke |
| 8,188,266 B2 | 5/2012 | Edelmann et al. |
| 8,298,679 B2 | 10/2012 | Albert et al. |
| 8,394,972 B2 | 3/2013 | Wassmer et al. |
| 8,481,165 B2 | 7/2013 | Edelmann et al. |
| 8,728,225 B2 | 5/2014 | Standke et al. |
| 8,747,541 B2 | 6/2014 | Scharfe et al. |
| 8,864,895 B2 | 10/2014 | Albert et al. |
| 2006/0247329 A1 | 11/2006 | Moszner et al. |
| 2008/0206572 A1 | 8/2008 | Edelmann et al. |
| 2009/0005518 A1 | 1/2009 | Just et al. |
| 2009/0007818 A1 | 1/2009 | Militz et al. |
| 2012/0321803 A1 | 12/2012 | Borup et al. |
| 2013/0167754 A1 | 7/2013 | Wassmer et al. |

FOREIGN PATENT DOCUMENTS

| | | |
|---|---|---|
| EP | 2 277 496 | 1/2011 |
| JP | 5-25219 A | 2/1993 |
| JP | 2003-501435 A | 1/2003 |
| JP | 2006-306871 A | 11/2006 |
| JP | 2012-505822 A | 3/2012 |
| WO | 00 75148 | 12/2000 |
| WO | WO 2013/156185 A1 | 10/2013 |
| WO | WO 2013/156187 A1 | 10/2013 |

OTHER PUBLICATIONS

U.S. Appl. No. 14/395,750, filed Oct. 20, 2014, Wassmer, et al.
U.S. Appl. No. 14/395,598, filed Oct. 20, 2014, Wassmer, et al.
Boonlom Thavornyutikarn et al., "Synthesis and Characterization of UV-Curable Poly(dimethylsiloxane) Dimethacrylate", Macromolecular Symposia, vol. 264, No. 1, Total 5 Pages, (Apr. 1, 2008) XP0055064752.
International Search Report Issued Jun. 11, 2013 in PCT/EP13/053674 Filed Feb. 25, 2013.
Search Results Issued in the Priority Application DE 10 2012 206 509.1 Filed Apr. 20, 2012.

*Primary Examiner* — Porfirio Nazario Gonzalez
(74) *Attorney, Agent, or Firm* — Oblon, McClelland, Maier & Neustadt, L.L.P.

(57) ABSTRACT

The invention relates to a process for preparing (meth)acrylamido-functional silanes.

19 Claims, No Drawings

PROCESS FOR PREPARING (METH)ACRYLAMIDO-FUNCTIONAL SILANES BY THE REACTION OF AMINOALKYL ALKOXYSILANES WITH ACRYLIC ACID ANHYDRIDE

CROSS-REFERENCE TO RELATED APPLICATIONS

This application is a National Stage of PCT/EP2013/053674 filed on Feb. 25, 2013. This application is based upon and claims the benefit of priority to German Application No. 10 2012 206 509.1 filed on Apr. 20, 2012.

The invention relates to a process for preparing (meth)acrylamido-functional silanes and to formulations comprising them.

For the use of glass fibres in fibre composite materials, the glass fibre is frequently surface-treated with functionalized silanes. This is commonly accomplished with the aid of aqueous slips in which the organofunctional silane is dissolved. Depending on the chemical function of the silanes, there may be a positive influence on the desired properties, for example fibre thickness or else cuttability (specifically for short fibre reinforcement). In this case, the organofunctional silanes also make a significant contribution to promoting adhesion between the inorganic fibre and the organic resin. Even though application by means of aqueous slips is desirable, the organofunctional silanes are still prepared in organic solvents.

For example, specific methacryloyl-functionalized silanes, for example 3-methacryloyloxypropyltrimethoxysilane, are used in fibre composite materials, examples being thermosets and thermoplastics, in order to increase the performance of the fibre composite material. In other applications too, such as in filler modification, in coatings or in adhesives/sealants, these functionalized silanes are used as adhesion promoter between organic and inorganic matrix. In addition, methacryloyl-functionalized silanes are used for production of synthetic stone. For this purpose, these silanes together with unsaturated polyester resins (UPE resin) and silicon-containing natural rock, such as quartz sand and/or quartz flour, are made into appropriate synthetic stone slabs.

A further application lies in the modification of specific properties, for example increasing the cuttability of glass fibres. Some compounds used for that purpose are methacrylamidoalkylalkoxysilanes such as $(RO)_xRSiNH(CO)C(CH_3)=CH_2$ or else chromium(III) methacrylate chlorine complexes, for example Volan® from DuPont (R=C1-C6 alkyl group).

WO 00/75148 A1 (comparative example 1 here) describes a synthesis proceeding from aminopropyltriethoxysilane with a methyl methacrylate in the presence of dibutyltin oxide (DBTO). This reaction has a number of disadvantages: firstly, for a substantially complete conversion, a 100% excess of methacrylate is used, which has to be distilled off again. Thus, the space-time yield is poor. In addition, the reaction is conducted at high temperatures of 165-170° C., which results in problems because of the tendency of acrylic acid to polymerize. To avoid polymerization, a stabilizer has to be used. Catalysts used for essentially complete conversion are toxic, environmentally damaging organotin compounds, for example dibutyltin oxide (DBTO). A further disadvantage of this process is the costly and inconvenient rectification of the reaction product at high bottom temperatures and very low absolute pressure. For this purpose, a further gas phase stabilizer has to be used in order to avoid polymerization in the column. A heavy metal-containing residue remains in the bottoms, and has to be disposed of separately. The distillation product is the commercially available product Y-5997 from Momentive $(CH_3O)_x(C_2H_5O)_{3-x}Si(CH_2)_3NH(CO)C(CH_3)=CH_2$.

U.S. Pat. No. 3,249,461 describes the synthesis of methacrylamidopropylmethoxysilane by reaction of methacryloyl chloride in mixtures of anhydrous solvents containing aromatic hydrocarbons with aminopropyltrimethoxysilane and dinitrobenzene. Disadvantages in this process are the use of the solvent mixture containing aromatics and the release of an equimolar amount of hydrogen chloride, which has to be removed from the process in a costly and inconvenient manner. In addition, the solvent content reduces the space-time yield. The use of dinitrobenzene as a stabilizer is also problematic.

The problem addressed by the present invention was that of providing environmentally friendly processes for preparing (meth)acrylamido-functional silanes in which less, preferably no, organic solvents are used and which give good conversions without the use of toxic compounds such as organic tin compounds. Equally, the use of stabilizers, as is necessary in the prior art, was to be reduced; preferably, a process which manages without the use of stabilizers was to be found. A further problem was to discover a process which allows preparation in the form of a one-pot reaction. Furthermore, a formulation for the acrylamido-functional silanes thus prepared was to be developed. Moreover, the problem was to develop a process which manages without the use of chlorine-containing compounds.

The problems were solved by a process according to Claim 1 and a formulation according to Claim 16, with the elucidation of preferred embodiments in the dependent claims and in the description.

The problem was likewise solved by a controlled anhydrous, and preferably diluent-free or solvent-free, conversion of aminosilanes under temperature control in the presence of acrylic anhydride. Preferred aminosilanes are aminoalkylalkoxysilanes, preferably di- and/or triaminoalkyl-functional silanes. Particular preference is given to reacting 3-aminopropyltrialkoxysilane or N-(2-aminoethyl)-3-aminopropyltrialkoxysilane in approximately equimolar amounts with acrylic anhydride, especially (meth)acrylic anhydride, directly, preferably under temperature control, to give the acrylamides. Temperature control is understood to mean the maintenance of a temperature range during the reaction between about 15 and 50° C., preferably 20 and 40° C., further preferably 20 and 35° C., since it is preferably possible within this range to dispense with the addition of stabilizers. Consequently, the invention provides a process consisting of the reaction of aminoalkylalkoxysilanes with acrylic anhydride under temperature control and with optional removal of the acrylic acid released or of the reaction products thereof. The acrylamidoalkylsilanes thus prepared can subsequently, if required, be hydrolysed and/or condensed directly to oligomeric siloxanes or siloxanols, and be diluted as desired.

It is a great advantage of the invention that the acrylamidoalkyl-functional silanes thus obtained can preferably be used in the form of the bottom product without further purification. It is thus possible through the process according to the invention to supply acrylamido-functional silanes and mixtures of these, especially (meth)acrylamidoalkyl-functional alkoxysilanes, as products prepared in a particularly economically viable and environmentally responsible manner. It is possible to dispense with a costly and inconvenient distillative removal of solvents and diluents.

The invention provides a process for preparing acrylamidoalkyl-functional silanes and mixtures of these, by reacting an aminoalkyl-functional alkoxysilane of the formula I or a mixture comprising at least two silanes of the formula I $$(R^1O)_{3-a-b}(R^2)_a Si(B)_{1+b} \qquad (I)$$

where the group B in formula I independently corresponds to a group of the formula II $$-(CH_2)_c-[(NH)(CH_2)_d]_e[(NH)](CH_2)_f]_g NH_{(2-h)}R^3{}_h \qquad (II).$$

in formula I with $R^1$ independently a linear, branched or cyclic alkyl group having 1 to 8 carbon atoms, especially having 1, 2, 3 or 4 carbon atoms, $R^2$ independently a linear, branched or cyclic alkyl group having 1 to 8 carbon atoms, and in formula II with $R^3$ independently a linear, branched or cyclic alkyl, aryl or alkylaryl group having 1 to 8 carbon atoms; and in formula I a is independently 0 or 1, a preferably being 0, b is independently 0, 1 or 2, b preferably being 0, in formula II c is independently selected from 1, 2, 3, 4, 5 and 6, d is independently selected from 1, 2, 3, 4, 5 and 6, e is independently selected from 0, 1, 2, 3, 4, 5 and 6, f is independently selected from 1, 2, 3, 4, 5 and 6, g is independently selected from 0, 1, 2, 3, 4, 5 and 6, and h is independently 0 or 1, or the B group in formula I corresponds to a group of the formula III, with j=1, 2 or 3 and p=0, 1 or 2, p preferably being selected from 0 and 1, $$-(CH_2)_j-NH_{2-p}(CH_2-CH_2-NH_2)_p \qquad (III)$$

with acrylic anhydride of the formula IV $$(CHR^5{=}CR^4CO)_2O \qquad (IV)$$

where $R^4$ is independently a hydrogen atom or a methyl group and $R^5$ is independently a hydrogen atom or a methyl group, $R^5$ preferably being a hydrogen atom, and acrylic acid or reaction products of acrylic acid are optionally removed.

In a preferred process variant, the process consists of the aforementioned steps. In addition, it is equally preferable to conduct the process preferably essentially in the absence of solvent or diluent and preferably without stabilizers, under temperature control. A process is considered to be "essentially in the absence of solvents or diluents" in that the content of solvents or diluents during the reaction or in the reaction mixture or in the overall composition is less than or equal to 1.5% by weight, preferably less than or equal to 0.5% by weight, more preferably less than or equal to 0.1% by weight down to the detection limit. In this context, alcohol of hydrolysis released from the alkoxysilane as a result of the reaction is not considered to be a solvent or diluent.

A reaction is considered to be an anhydrous reaction when the water content during the reaction or in the reaction mixture, or synonymously the overall composition, is less than or equal to 1% by weight, preferably less than or equal to 0.5% by weight, especially 0.25% by weight, preferably less than or equal to 0.1% by weight, more preferably less than or equal to 0.001% by weight to 0.000001% by weight. The reaction is preferably considered to be anhydrous when the water content is less than or equal to 1 ppm by weight, especially less than or equal to 0.1 ppm by weight.

In the course of performance of the process, it is especially preferable to conduct the reaction at a temperature below 80° C., especially below 50° C., preferably below 45° C., more preferably below 40° C., especially preferably below 35° C. to greater than or equal to 0° C., including all the temperature values inbetween. Particular preference is given to a process wherein the reaction is effected within a defined temperature range, preferably below 50° C., more preferably below 40° C., in the absence of a stabilizer.

By the process according to the invention, preferably acrylamidoalkyl-functional silanes of the general formula V or mixtures of these are prepared $$(R^1O)_{3-a-b}(R^2)_a Si(C)_{1+b} \qquad (V)$$

with $R^1$ independently a linear, branched or cyclic alkyl group having 1 to 8 carbon atoms, especially having 1, 2, 3 or 4 carbon atoms, or acryloylcarbonyl such as $-(CO)R^4C{=}CR^5H$, and $R^2$ independently a linear, branched or cyclic alkyl group having 1 to 8 carbon atoms, and the C group being an acrylamidoalkyl-functional group, with a independently 0 or 1, b independently 0, 1 or 2, b preferably being 0, in which case a is preferably also 0. It is further preferable when the acrylamidoalkyl-functional C group is selected from $-(CH_2)_c-[(NH)(CH_2)_d]_e[(NH)](CH_2)_f]_g NH_{(1-h)}R^3{}_h-(CO)CR^4{=}CHR^5$, $-(CH_2)_j-NH(CH_2-CH_2-NH)-(CO)CR^4{=}CHR^5$ and $-(CH_2)_j-NH_{2-p}(CH_2-CH_2-NH-(CO)CR^4{=}CHR^5)_p$, where c, d, e, f, g, h, j, p and $R^3$, $R^4$, $R^5$ are each as defined above or below.

In a particularly preferred process variant, the acrylic acid and/or reaction products thereof are removed by means of distillation, formation of a soluble or insoluble compound or chromatography, especially flash chromatography, or a combination of the aforementioned measures. Equally preferably, the acrylic acid released can be masked by addition of complexing agents.

In a particularly gentle manner, the distillation can be effected under reduced pressure, for example between 0.001 and 800 mbar, in a standard distillation column, short-path distillation column or thin-film evaporator. The distillation is preferably conducted at a bottom temperature below 150° C., preferably below 120° C. Preference is further given to bottom temperatures below 100° C.

To form insoluble compounds, it is generally possible to very effectively form co-crystals with the acrylic acid or else insoluble salts with the acrylic acid released. The advantage of the formation of insoluble compounds is that they bind acrylic acid released directly during the reaction and hence the formation of transesterification products can be prevented.

Because of the temperature control and any further cooling, insoluble compounds can be removed easily by means of decanting or filtration. To form soluble or insoluble co-crystals, also referred to as complexes in earlier literature, or insoluble salts, it is possible to use, by way of example, tertiary amines and/or heteroaromatics containing nitrogen atoms, preferably sterically hindered compounds. Examples of these are trialkylamines, preferably having branched alkyl groups having 1 to 8 carbon atoms, such as triethylamine, tripropylamine, tributylamine, or N-heteroaromatics such as acridine, phenazine or pyridine. The tertiary amines may, however, also be present bound to a solid phase. Phenazine can bind two acrylic acids.

In a preferred alternative, the acrylic acid is not removed during or after the reaction when aminoalkyl-functional silanes of the formula I having secondary and/or tertiary nitrogen atoms are used in the process.

The invention likewise provides a process wherein
in a step (I), an aminoalkyl-functional alkoxysilane of the formula I is converted with
addition of a defined amount of acrylic anhydride of the formula IV and the acrylic anhydride of the formula IV is preferably metered in such that the temperature of the mixture does not rise above 40° C., especially not above 40° C., preference being given to cooling, and under temperature control, preferably below 50° C., more preferably below 40° C., and acrylic acid is removed in step (II). The bottom temperature in the course of reaction with (meth)acrylic anhydride can be controlled via the rate of dropwise addition of (meth)acrylic anhydride. By cooling the reactor, it is possible to achieve quicker addition of (meth)acrylic acid.

In addition, it may be preferable when, in one process variant, the reaction is effected in the presence of an anhydrous aprotic or organic protic solvent at a temperature below 40° C., especially in the absence of a stabilizer. It may likewise be preferable to conduct the reaction in the presence of an anhydrous aprotic or organic protic solvent or solvent mixture, in which case at least one solvent forms insoluble compounds or stable complexes with the acrylic acid.

In general, the solvents may be selected from ketones, secondary amines, tertiary amines, nitrogen-containing heteroaromatics, DMFA, especially trialkylamines such as triethylamine, tributylamine, piperidine, preference being given to sterically hindered amines. The complexing agent is preferably used in an approximately equimolar amount or in excess relative to the acrylic acid released. An anhydrous solvent is considered to be a solvent having a water content of less than or equal to 1% by weight, especially less than or equal to 0.5% by weight, preferably less than or equal to 0.1% by weight, more preferably less than or equal to 0.01% by weight to 0.00001% by weight. Preferably, a solvent having a water content of less than 1 ppm by weight is considered to be anhydrous.

It has been found that, in the direct reaction of aminosilanes with acrylic anhydride, transesterification products also occur. The formation thereof can be controlled by the temperature control or the addition of complexing agents or compounds which scavenge the acrylic acid.

The active ingredient content of the silanes prepared is preferably up to 100% by weight, especially already in the form of the bottom product. Furthermore, they are preferably free of water and solvent and/or diluent resulting from preparation. According to the process regime, the silanes may have a certain content of silanols or oligomeric siloxanes/siloxanols. Likewise preferably, it is possible to obtain silanes having a low content of diluent of up to 5% by weight. In the later use, the active ingredient content of the silanes can be adjusted as desired.

According to the invention, it is possible in principle to use all aminoalkoxysilanes as a mixture too for preparation of the acrylamido-functional silanes. One advantage of the di- and triaminosilanes is that they have a primary amino group and at least one secondary amino group capable of neutralizing the (meth)acrylic acid released in the reaction to form a corresponding salt (aminohydromethacrylate). The aminohydro(meth)acrylate can be cleaved under basic conditions. Suitable bases are preferably basic alkali metal salts such as NaOH or KOH, preferably alkali metal alkoxides such as NaOR or KOR, preferably where R=alkyl-, preferably methyl-, and particular preference being given to potassium methoxide. When potassium methoxide is used, the methacrylic acid is precipitated as potassium methacrylate and can be removed easily by filtration.

Preferred aminoalkyl-functional alkoxysilanes correspond to the formula I where the group B in formula I independently corresponds to a group of the formula II with $R^1$ independently a linear, branched or cyclic alkyl group having 1 to 8 carbon atoms, especially having 1, 2, 3 or 4 carbon atoms, preferably methyl, ethyl or propyl, and $R^2$ independently a linear, branched or cyclic alkyl group having 1 to 8 carbon atoms, especially methyl, ethyl, propyl, n-butyl, isobutyl, tert-butyl, pentyl, hexyl, heptyl or octyl, and in formula II with $R^3$ independently a linear, branched or cyclic alkyl, aryl or alkylaryl group having 1 to 8 carbon atoms, especially methyl, ethyl, butyl or benzyl, where h=0 is particularly preferred; and in formula I a is independently 0 or 1, b is independently 0, 1 or 2, b preferably being 0, and in formula II c is independently selected from 1, 2, 3, 4, 5 and 6, d is independently selected from 1, 2, 3, 4, 5 and 6, e is independently selected from 0, 1, 2, 3, 4, 5 and 6, f is independently selected from 1, 2, 3, 4, 5 and 6, g is independently selected from 0, 1, 2, 3, 4, 5 and 6, and h is independently 0 or 1; alternatively preferably e=g=0 or 1, and d=f=2 or 3 and h=0 with c=3 and b=0 and a=0; particularly preferred combinations are with $R^1$ being methyl or ethyl, a=0 and b=0 with c=3 and g, e and h each=0; alternatively likewise preferably, a=0, b=0, c=3, e=1, d=1, 2 or 3, preferably d=2, and g=0, h=0, for diaminofunctional silanes, or the B group corresponds to the formula III with j=1, 2 or 3 and p=0, 1 or 2, p preferably being selected from 1 and 2, and it may also be appropriate that p=0.

It is generally preferable, in one process variant, when the aminoalkyl-functional alkoxysilane corresponds to a diaminoalkyl-functional or a triaminoalkyl-functional silane, preferably a diaminoalkyl-functional or a triaminoalkyl-functional alkoxysilane of the formula I. Likewise particularly preferred are mixtures of the aforementioned silanes, such as aminosilane with diaminosilane or else aminosilane with triaminosilane or diaminosilane with triaminosilane, or else mixtures comprising three or more different aminosilanes of the formula I.

The acrylic anhydrides used are preferably (meth)acrylic acid or acrylic anhydride, more preferably of the formula IV $$(CHR^5=CR^4CO)_2O \tag{IV}$$

where $R^4$ is independently a hydrogen atom or a methyl group and $R^5$ is independently a hydrogen atom or a methyl group, $R^5$ preferably being a hydrogen atom. Preference is given to $(CH_2=C(CH_3)CO)_2O$ and $(CH_2=CHCO)_2O$.

According to the invention, it is unnecessary to further purify acrylamido-functional silanes obtained after the reaction; optionally, the acrylic acid can be removed or masked; more particularly, a complex distillative workup, such as rectification, of the acrylamido-functional silanes is unnecessary, since the bottom products can preferably be used directly. The inventive bottom products do not require any further purification since no disruptive catalysts or disruptive stabilizers are present in the bottom products. This is because a particular advantage of the process according to the invention is the lack of stabilizers and gas phase stabilizers, as necessary in the prior art. Consequently, the process according to the invention is much more economically viable and can be conducted with more environmentally compatible starting substances than known processes.

In preferred embodiments, the process is preferably conducted with an aminoalkyl-functional alkoxysilane of the formula I a) with $R^1$ independently methyl or ethyl and with a=0 and b=0 with c=1, 2 or 3 and with the group B of the formula II with g=0 and e=1 and h=0, d=1, 2, 3, preferably d=2, or b) with $R^1$ independently methyl or ethyl and with a=0 and b=0 with c=3 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=3 or with the group B of the formula III with j=3 and p=1 or 2, or c) with $R^1$ independently methyl or ethyl and with a=0 and b=0 with c=2 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=2 or with the group B of the formula III with j=3 and p=1 or 2, or d) with $R^1$ independently methyl or ethyl and with a=0 and b=0 with c=1 and with the group B of the formula II with g, e and h each 0 or, in an alternative, with a=0, b=0, c=3, and with the group B of the formula II with e=1, d=1, 2, 3, preferably d=2 and with g=0, h=0 or with the group B of the formula II with e=g=0 or 1, and d=f=2 or 3 and h=0 with c=1 or with the group B of the formula III with j=3 and p=1 or 2.

It is likewise preferable when the process is preferably conducted with an aminoalkyl-functional alkoxysilane of the general formula I, selected from the following silanes: 3-aminopropyltrimethoxysilane, 3-aminopropyltriethoxysilane, 3-aminopropylmethyldimethoxysilane, 3-aminopropylmethyldiethoxysilane, 1-aminomethyltrimethoxysilane, 1-aminomethyltriethoxysilane, 2-aminoethyltrimethoxysilane, 2-aminoethyltriethoxysilane, 3-aminoisobutyltrimethoxysilane, 3-aminoisobutyltriethoxysilane, N-n-butyl-3-aminopropyltriethoxysilane, N-n-butyl-3-aminopropylmethyldiethoxysilane, N-n-butyl-3-aminopropyltrimethoxysilane, N-n-butyl-3-aminopropylmethyldimethoxysilane, N-n-butyl-1-aminomethyltriethoxysilane, N-n-butyl-1-aminomethylmethyldimethoxysilane, N-n-butyl-1-aminomethyltrimethoxysilane, N-n-butyl-1-aminomethylmethyltriethoxysilane, benzyl-3-aminopropyltrimethoxysilane, benzyl-3-aminopropyltriethoxysilane, benzyl-2-aminoethyl-3-aminopropyltrimethoxysilane, benzyl-2-aminoethyl-3-aminopropyltriethoxysilane, diaminoethylene-3-propyltrimethoxysilane, diaminoethylene-3-propyltriethoxysilane, triaminodiethylene-3-propyltrimethoxysilane, triaminodiethylene-3-propyltriethoxysilane, (2-aminoethylamino)ethyltrimethoxysilane, (2-aminoethylamino)ethyltriethoxysilane, (1-aminoethylamino)methyltrimethoxysilane and (1-aminoethylamino)methyltriethoxysilane, preference being given especially to di- and/or triaminoalkoxysilanes. Particular preference is given to diaminoethylene-3-propyltrimethoxysilane, diaminoethylene-3-propyltriethoxysilane, triaminodiethylene-3-propyltrimethoxysilane, triaminodiethylene-3-propyltriethoxysilane.

Preferably, in the process, the molar ratio of the nitrogen atoms in the aminoalkyl-functional silanes to the molar ratio of the $CHR^5$=$CR^4$(CO)— acryloylcarbonyl function released from the acrylic anhydride of the formula I is set within the range from 1:5 to 5:1, and is especially 1:2 to 2:1, preferably 1:1.5 to 1.5:1, more preferably 1:1 with a range of variation of plus/minus 0.5, preferably plus/minus 0.2. Alternatively, it may be particularly preferable to use a diaminoalkyl-functional silane in an equimolar amount with acrylic anhydride of the formula I. The secondary amino function here can neutralize the free acrylic acid, and can react to give an aminohydromethacrylate, which can subsequently be cleaved under basic conditions.

The invention also provides a formulation comprising a process product and at least one further formulation constituent selected from auxiliary, polymer, water, diluent, additive, pigment, filler, acid, base or buffer. Polymers used in the formulation may preferably be silane-terminated polyurethanes. Further formulation constituents may be plasticizers, catalysts, crosslinkers and/or water scavengers. It is likewise possible to add standard stabilizers to increase the storage stability.

The acrylamidoalkyl-functional silanes prepared in accordance with the invention can preferably be used as an adhesion promoter, for functionalization of glass, especially for functionalization of glass fibres, for modification of fillers, pigments, organic surfaces and/or inorganic surfaces, especially as a filler coating, where the fillers may be inorganic or organic fillers, coating of pigments, coating of organic or inorganic surfaces, in formulations, in dental impression compounds, in dental polymer compounds, as an additive in polymers, in adhesives, in sealants, in fibre composite materials, together with monomers or polymers, especially thermoplastics, thermosets, elastomers, for functionalization of polymers, for adjusting the profile of properties of polymers, for production of masterbatches, as an additive in resin systems, especially in unsaturated organic resin systems, such as alkyd resins. Such as for production of synthetic stone. Particular preference is given to use for attachment/binding of inorganic materials to organic materials, especially unsaturated organic materials. It is likewise possible to use the silanes for production of masterbatches.

In summary, it can be stated that the process according to the invention is notable in that it is particularly environmentally friendly and can be operated with very good space-time yield, since it is based on the pure conversion of the aminoalkylsilanes with acrylic anhydride as a one-pot process, and does not require the use of heavy metals, such as chromium, or the use of tin compounds. Furthermore, it is possible to dispense with the use of chlorine-containing compounds.

The following examples illustrate the process according to the invention in more detail without limiting the invention to these examples.

Determination Methods:

The alcohol content after hydrolysis is determined by gas chromatography (% by weight). $SiO_2$ content of organic silicon compounds: determined by processes known to those skilled in the art, for example oxidation of the organic constituents, followed by calcination, hydrofluoric acid fuming and determination of the weight difference (%=% by weight). Determination of nitrogen: By a method known to those skilled in the art, for example according to Kjeldahl.

EXAMPLE 1

A 500 ml stirred apparatus with distillation system was initially charged with 88.81 g of aminopropyltriethoxysilane (0.401 mol) and 34.80 g of aminopropyltrimethoxysilane (AMMO) (0.194 mol). 92.61 g of methacrylic anhydride (0.6 mol) were added dropwise while cooling by means of an ice bath within 1 hour. In the course of this, the bottom temperature rose to max. 32.0° C. Subsequently, some of the free methacrylic acid was distilled off at an absolute pressure of 6 mbar up to a bottom temperature of 115° C. 175.8 g of pale yellowish bottom product were obtained.

TABLE 1

Analysis results for the bottom product from Example 1

| Determination | Method | Result |
|---|---|---|
| Total N [%] | see above | 4.4 |
| SiO$_2$ content [%] | see above | 19.4 |
| pH | DIN ISO 4925 | 5.5 |
| Viscosity [mPa · s] | DIN 53015 | 447 |
| $^1$H and $^{13}$C NMR | Quantitative evaluation shows:<br>43 mol % of methacrylamidopropylmethoxy-diethoxysilane<br>57 mol % of methacrylamidopropyldialkoxy-carboxysilane* | |
| $^{29}$Si NMR | No oligomers are detectable | |

*carboxy = methacrylic ester

COMPARATIVE EXAMPLE 1

Comparative Example According to WO 00/75148 A1

A 1 l stirred apparatus with distillation system was initially charged with 398.07 g of aminopropyltriethoxysilane (1.8 mol), and 1.99 g of dibutyltin oxide, 0.037 g of ionol and 0.18 g of 4,4'-thiobis(6-tert-butyl-m-cresol) were stirred in. Subsequently, within 2 hours, a mixture of 360.35 g of methyl methacrylate (3.60 mol) and 5.41 g of dipropylamine was metered in at a bottom temperature of 152.8° C. to 165.5° C. After a reaction time of 0.3 hour, at a top temperature of 76.5° C. to 80.4° C., a mixture of methanol, ethanol, methyl methacrylate and ethyl methacrylate was removed. After a distillation time of 2.5 hours, at an absolute pressure of 316 mbar to <1 mbar and a bottom temperature of 157.2° C., residual amounts of low boilers were removed from the bottom product. A total of 287.8 g of distillate was removed. 461.35 g of pale yellowish and low-viscosity liquid were obtained as the bottom product. In accordance with the disclosure of WO 00/75148 A1, the crude methacrylic product is distilled under high vacuum. This was omitted in the present example.

TABLE 2

Analysis results from Comparative Example 1

| Determination | Method | Result |
|---|---|---|
| Total N [%] | see above | 5.0 |
| SiO$_2$ content [%] | see above | 22.0 |
| pH | DIN ISO 4925 | 9.7 |
| Viscosity [mPa · s] | DIN 53015 | 50.1 |

Table 3 shows the analysis results for the commercially available Y-5997.

TABLE 3

Analysis results for Y-5997

| Determination | Method | Result |
|---|---|---|
| Total N [%] | see above | 4.9 |
| SiO$_2$ content [%] | see above | 21.9 |
| pH | DIN ISO 4925 | 9.0 |
| Viscosity [mPa · s] | DIN 53015 | 35.0 |
| $^1$H and $^{13}$C NMR | Show the trialkoxysilylpropyl methacrylate<br>66.4 mol % SiOC$_2$H$_5$<br>1.0 mol % ethanol<br>31.9 mol % SiOCH$_3$ | |
| $^{13}$C NMR | 0.7 mol % methanol | |

The invention claimed is:

1. A process for preparing an acrylamidoalkyl-functional silane, the process comprising:
    reacting an aminoalkyl-functional alkoxysilane of formula I or a mixture comprising at least two silanes of the formula I with an acrylic anhydride of formula IV to obtain an intermediate reaction product:

$$(R^1O)_{3-a-b}(R^2)_a Si(B)_{1+b} \quad (I)$$

$$(CHR^5 = CR^4 CO)_2 O \quad (IV); \text{ and}$$

optionally partially removing an acrylic acid and/or reaction products of the acrylic acid from the intermediate reaction product, to form the acrylamidoalkyl-functional silane, wherein:
R$^4$ is independently a hydrogen atom or a methyl group and R$^5$ is independently a hydrogen atom or a methyl group;
R$^1$ is independently a linear, branched or cyclic alkyl group having 1 to 8 carbon atoms;
R$^2$ is independently a linear, branched or cyclic alkyl group having 1 to 8 carbon atoms;
a is independently 0 or 1;
b is independently 0, 1 or 2; and
group B is independently a group of formula II or a group of formula III $$-(CH_2)_c-[(NH)(CH_2)_d]_e[(NH)](CH_2)_f]_g NH_{(2-h)} R^3_h \quad (II)$$

$$-(CH_2)_f-NH_{2-p}(CH_2-CH_2-NH_2)_p \quad (III),$$

wherein:
R$^3$ is independently a linear, branched or cyclic alkyl, aryl or alkylaryl group having 1 to 8 carbon atoms;
c is independently selected from 1, 2, 3, 4, 5 and 6;
d is independently selected from 1, 2, 3, 4, 5 and 6;
e is independently selected from 0, 1, 2, 3, 4, 5 and 6;
f is independently selected from 1, 2, 3, 4, 5 and 6;
g is independently selected from 0, 1, 2, 3, 4, 5 and 6;
h is independently 0 or 1;
j=1, 2 or 3 and
p=0, 1 or 2.

2. The process according to claim 1, wherein the reacting occurs at a temperature below 80° C.

3. The process according to claim 1, wherein the reacting occurs essentially in the absence of a solvent or diluent, such that the solvent or diluent content in the overall composition is less than or equal to 0.5% by weight.

4. The process according to claim 1, wherein the reacting occurs within a temperature range below 50° C., and in the absence of a stabilizer.

5. The process according to claim 1, wherein the reacting occurs in the presence of an anhydrous aprotic or organic protic solvent at a temperature below 40° C.

6. The process according to claim 1, wherein in the aminoalkyl-functional alkoxysilane of formula I:
    a) R$^1$ is independently methyl or ethyl where a=0, b=0, c=1, 2 or 3 and group B is of formula II where g=0, e=1 h=0, and d=1, 2, 3;
    b) R$^1$ is independently methyl or ethyl where a=0, b=0, c=3 and group B is of formula II where g, e and h each 0 or, in an alternative, a=0, b=0, c=3, and group B is of formula II where e=1, d=1, 2, 3, g=0, h=0 or group B is of formula II where e=g=0 or 1, and d=f=2 or 3 and h=0 with c=3 or group B is of formula III where j=3 and p=1 or 2;
    c) R$^1$ is independently methyl or ethyl where a=0, b=0, c=2 and group B is of formula II where g, e and h each 0 or, in an alternative, where a=0, b=0, c=3, and group B is of formula II where e=1, d=1, 2, 3, and g=0, h=0 or group B is of formula II where e=g=0 or 1, and d=f=2 or 3 and h=0 with c=2 or group B is of formula III where j=3 and p=1 or 2; or d) $R^1$ is independently methyl or ethyl where a=0 and b=0 with c=1 and group B is of formula II where g, e and h each 0 or, in an alternative, where a=0, b=0, c=3, and group B is of formula II where e=1, d=1, 2, 3, and with g=0, h=0 or group B is of formula II with e=g=0 or 1, and d=f=2 or 3 and h=0 with c=1 or group B is of formula III where j=3 and p=1 or 2.

7. The process according to claim 1, wherein the aminoalkyl-functional silane of the formula I is selected from the group consisting of 3-aminopropyltrimethoxysilane, 3-aminopropyltriethoxysilane, 3-aminopropylmethyldimethoxysilane, 3-aminopropylmethyldiethoxysilane, 1-aminomethyltrimethoxysilane, 1-aminomethyltriethoxysilane, 2-aminoethyltrimethoxysilane, 2-aminoethyltriethoxysilane, 3-aminoisobutyltrimethoxysilane, 3-aminoisobutyltriethoxysilane, N-n-butyl-3-aminopropyltriethoxysilane, N-n-butyl-3-aminopropylmethyldiethoxysilane, N-n-butyl-3-aminopropyltrimethoxysilane, N-n-butyl-3-aminopropylmethyldimethoxysilane, N-n-butyl-1-aminomethyltriethoxysilane, N-n-butyl-1-aminomethylmethyldimethoxysilane, N-n-butyl-1-aminomethyltrimethoxysilane, N-n-butyl-1-aminomethylmethyltriethoxysilane, benzyl-3-aminopropyltrimethoxysilane, benzyl-3-aminopropyltriethoxysilane, benzyl-2-aminoethyl-3-aminopropyltrimethoxysilane, benzyl-2-aminoethyl-3-aminopropyltriethoxysilane, diaminoethylene-3-propyltrimethoxysilane, diaminoethylene-3-propyltriethoxysilane, triaminodiethylene-3-propyltrimethoxysilane, triaminodiethylene-3-propyltriethoxysilane, (2-aminoethylamino)ethyltrimethoxysilane, (2-aminoethylamino)ethyltriethoxysilane, (1-aminoethylamino)methyltrimethoxysilane and (1-aminoethylamino)methyltriethoxysilane.

8. The process according to claim 1, wherein the acrylic anhydride of formula IV is methacrylic anhydride or (unsubstituted) acrylic anhydride.

9. The process according to claim 1, wherein a molar ratio of nitrogen atoms in the aminoalkyl-functional alkoxysilanes of formula I to a molar ratio of the acryloylcarbonyl function released from the acrylic anhydride of formula IV is from 1:5 to 5:1.

10. The process according to claim 1, wherein the acrylic acid is not removed in the case of reaction of aminoalkyl-functional silanes of formula I with secondary and/or tertiary nitrogen atoms.

11. The process according to claim 1, comprising:
converting the aminoalkyl-functional alkoxysilane of formula I with addition of a defined amount of acrylic anhydride of formula IV and under temperature control; and then
removing acrylic acid.

12. The process according to claim 1, wherein the acrylic acid is partially removed by distillation, formation of an insoluble compound or by chromatography, or is masked by addition of a complexing agent.

13. The process according to claim 1, wherein the reacting occurs in the presence of an anhydrous aprotic or organic protic solvent or solvent mixture, with a solvent forming insoluble compounds with the acrylic acid.

14. The process according to claim 1, wherein the acrylamidoalkyl-functional silane is of formula V:

$$(R^1O)_{3-a-b}(R^2)_a Si(C)_{1+b} \quad (V),$$

wherein:
$R^1$ is independently a linear, branched or cyclic alkyl group having 1 to 8 carbon atoms, or an acryloylcarbonyl of formula:

$$-(CO)R^4C=CR^5H;$$

$R^2$ is independently a linear, branched or cyclic alkyl group having 1 to 8 carbon atoms;
the C group is an acrylamidoalkyl-functional group;
a is independently 0 or 1; and
b is independently 0, 1 or 2.

15. The process according to claim 14, wherein the C group is selected from the group consisting of $$-(CH_2)_c-[(NH)(CH_2)_d]_e[(NH)(CH_2)_f]_g NH_{(1-h)}$$
$$R^3{}_h-(CO)CR^4=CHR^5,$$

$$-(CH_2)_f-NH(CH_2-CH_2-NH)-(CO)$$
$$CR^4=CHR^5, \text{ and}$$

$$-(CH_2)_f-NH_{2-p}(CH_2-CH_2-NH-(CO)$$
$$CR^4=CHR^5)_p.$$

16. A formulation comprising:
an acrylamidoalkyl-functional silane obtained by the process of claim 1;
at least one further formulation constituent selected from the group consisting of an auxiliary, a polymer, a diluent, an additive, a pigment, a filler, an acid, a base and a buffer; and
an acrylic acid.

17. The process according to claim 1, wherein the group B is of formula II.

18. The process according to claim 1, wherein the group B is of formula III.

19. The process according to claim 1, comprising removing acrylic acid and/or reaction products of acrylic acid from the intermediate reaction product.

* * * * *